United States Patent
Bouduban et al.

(10) Patent No.: US 10,022,121 B2
(45) Date of Patent: Jul. 17, 2018

(54) METHOD AND APPARATUS FOR GUIDING A SUTURE THREAD

(71) Applicant: DePuy Synthes Products, Inc., Raynham, MA (US)

(72) Inventors: Nicolas Bouduban, Zuchwil (CH); Alexander Ludin, Grenchen (CH)

(73) Assignee: DePuy Synthes Products, Inc., Raynham, MA (US)

( * ) Notice: Subject to any disclaimer, the term of this patent is extended or adjusted under 35 U.S.C. 154(b) by 271 days.

(21) Appl. No.: 14/831,359

(22) Filed: Aug. 20, 2015

(65) Prior Publication Data
US 2015/0351751 A1 Dec. 10, 2015

Related U.S. Application Data

(62) Division of application No. 13/271,697, filed on Oct. 12, 2011, now Pat. No. 9,226,745.

(60) Provisional application No. 61/392,601, filed on Oct. 13, 2010.

(51) Int. Cl.
*A61B 17/04* (2006.01)
*A61B 17/00* (2006.01)

(52) U.S. Cl.
CPC ...... *A61B 17/0469* (2013.01); *A61B 17/0482* (2013.01); *A61B 17/0483* (2013.01); *A61B 2017/00407* (2013.01); *A61B 2017/047* (2013.01); *A61B 2017/0496* (2013.01)

(58) Field of Classification Search
CPC ............ A61B 17/0469; A61B 17/0482; A61B 17/0483; A61B 2017/047
See application file for complete search history.

(56) References Cited

U.S. PATENT DOCUMENTS

| 919,138 | A | 4/1909 | Drake et al. |
|---|---|---|---|
| 2,625,934 | A | 1/1953 | Halliday |
| 3,013,559 | A | 12/1961 | Thomas |
| 3,892,240 | A | 7/1975 | Park |
| 4,224,947 | A | 9/1980 | Fukuda |
| 4,493,323 | A | 1/1985 | Albright et al. |
| 4,890,615 | A | 1/1990 | Caspari et al. |
| 5,254,126 | A | 10/1993 | Filipi et al. |
| 5,364,410 | A | 11/1994 | Failla et al. |
| 5,462,562 | A | 10/1995 | Elkus |

(Continued)

FOREIGN PATENT DOCUMENTS

| CN | 2164798 Y | 5/1994 |
|---|---|---|
| JP | 2008-188413 | 8/2008 |

(Continued)

OTHER PUBLICATIONS

English Translation of CN Office Action dated Mar. 30, 2017 for CN Application No. 201510686963.

*Primary Examiner* — Robert Lynch
(74) *Attorney, Agent, or Firm* — Baker & Hostetler LLP (57) ABSTRACT

A suture device is configured to guide a suture thread. The device includes a sleeve that defines an opening, and a plunger to which a suture thread can be attached. The plunger can be inserted into the opening of the sleeve, and movable between a retracted position and an advanced position. When the plunger is in the retracted position, a distal portion of the suture thread is located proximal with respect to the distal end of the suture device. When the plunger is in the advanced position, the distal portion of the suture thread is driven out the distal end of the suture device.

19 Claims, 7 Drawing Sheets

(56) References Cited

U.S. PATENT DOCUMENTS

| | | |
|---|---|---|
| 5,501,692 A | 3/1996 | Riza |
| 5,569,270 A | 10/1996 | Weng |
| 5,571,119 A | 11/1996 | Atala |
| 5,607,435 A | 3/1997 | Sachdeva et al. |
| 5,618,290 A | 4/1997 | Toy et al. |
| 5,681,333 A | 10/1997 | Burkhart et al. |
| 5,722,981 A | 3/1998 | Stevens |
| 5,741,278 A | 4/1998 | Stevens |
| 5,755,728 A | 5/1998 | Maki |
| 5,797,927 A | 8/1998 | Yoon |
| 5,910,148 A | 6/1999 | Reimels et al. |
| 6,090,063 A | 7/2000 | Makower et al. |
| 6,299,590 B1 | 10/2001 | Luscher et al. |
| 7,112,208 B2 | 9/2006 | Morris et al. |
| 7,615,059 B2 | 11/2009 | Watschke et al. |
| 7,699,857 B2 | 4/2010 | Kim |
| 7,842,050 B2 | 11/2010 | Diduch et al. |
| 2004/0254598 A1 | 12/2004 | Schumaker et al. |
| 2004/0267270 A1* | 12/2004 | Jacobs ............... A61B 17/0482 606/86 R |
| 2005/0283171 A1 | 12/2005 | Bellafore et al. |
| 2006/0271101 A1 | 11/2006 | Saadat et al. |
| 2007/0179510 A1 | 8/2007 | Stone |
| 2010/0049212 A1 | 2/2010 | Caborn et al. |
| 2010/0114123 A1 | 5/2010 | Nason |
| 2010/0137888 A1 | 6/2010 | Wulc et al. |
| 2010/0198235 A1 | 8/2010 | Pierce et al. |

FOREIGN PATENT DOCUMENTS

| | | | |
|---|---|---|---|
| WO | WO 2010095131 A1 * | 8/2010 | ......... A61B 17/0483 |
| WO | WO 2010/107698 | 9/2010 | |

\* cited by examiner

METHOD AND APPARATUS FOR GUIDING A SUTURE THREAD

CROSS-REFERENCE TO RELATED APPLICATIONS

This application is a divisional of U.S. application Ser. No. 13/271,697, filed Oct. 12, 2011, which claims the benefit of U.S. Patent Application Ser. No. 61/392,601 filed Oct. 13, 2010, the entire disclosures of which are hereby incorporated by reference herein.

FIELD OF THE DISCLOSURE

The present disclosure relates generally to a surgical device, and in particular relates to a suture device configured to guide a suture thread during a surgical treatment of human tissue.

BACKGROUND

One problem associated with conventional suture devices is that the insertion of the suture thread into the eye in the needle can be cumbersome and time consuming for the operator. Another problem with conventional suture devices is that they cannot handle both monofilament and braided suture in one instrument. This means that during a procedure an operator may have to switch between instruments in an inefficient and time consuming manner and also follow a complicated procedure simplification.

SUMMARY

In accordance with one embodiment, a suture device is configured to guide a suture thread. The suture device includes a sleeve and a plunger. The sleeve includes a sleeve body that defines a proximal end, and a distal end spaced from the proximal end along a central axis. The sleeve defines an opening that extends along the central axis between the proximal end and the distal end. The plunger includes a plunger body that extends along the central axis when the plunger is disposed in the opening of the sleeve. The plunger defines a clamp, the clamp including a pair of surfaces that are configured to capture the suture thread so as to releasably attach the suture thread to the plunger. The plunger is slidably disposed in the opening of the sleeve and movable distally from a first retracted position in which a distal portion of the suture thread is located in the suture device to a second advanced position in which the distal portion of the suture thread extends out of the suture device.

DESCRIPTION OF THE DRAWINGS

The foregoing summary, as well as the following detailed description of an example embodiment of the application, will be better understood when read in conjunction with the appended drawings, in which there is shown in the drawings an example embodiment for the purposes of illustration. It should be understood, however, that the application is not limited to the precise arrangements and instrumentalities shown. In the drawings.

DETAILED DESCRIPTION

Figure 1:
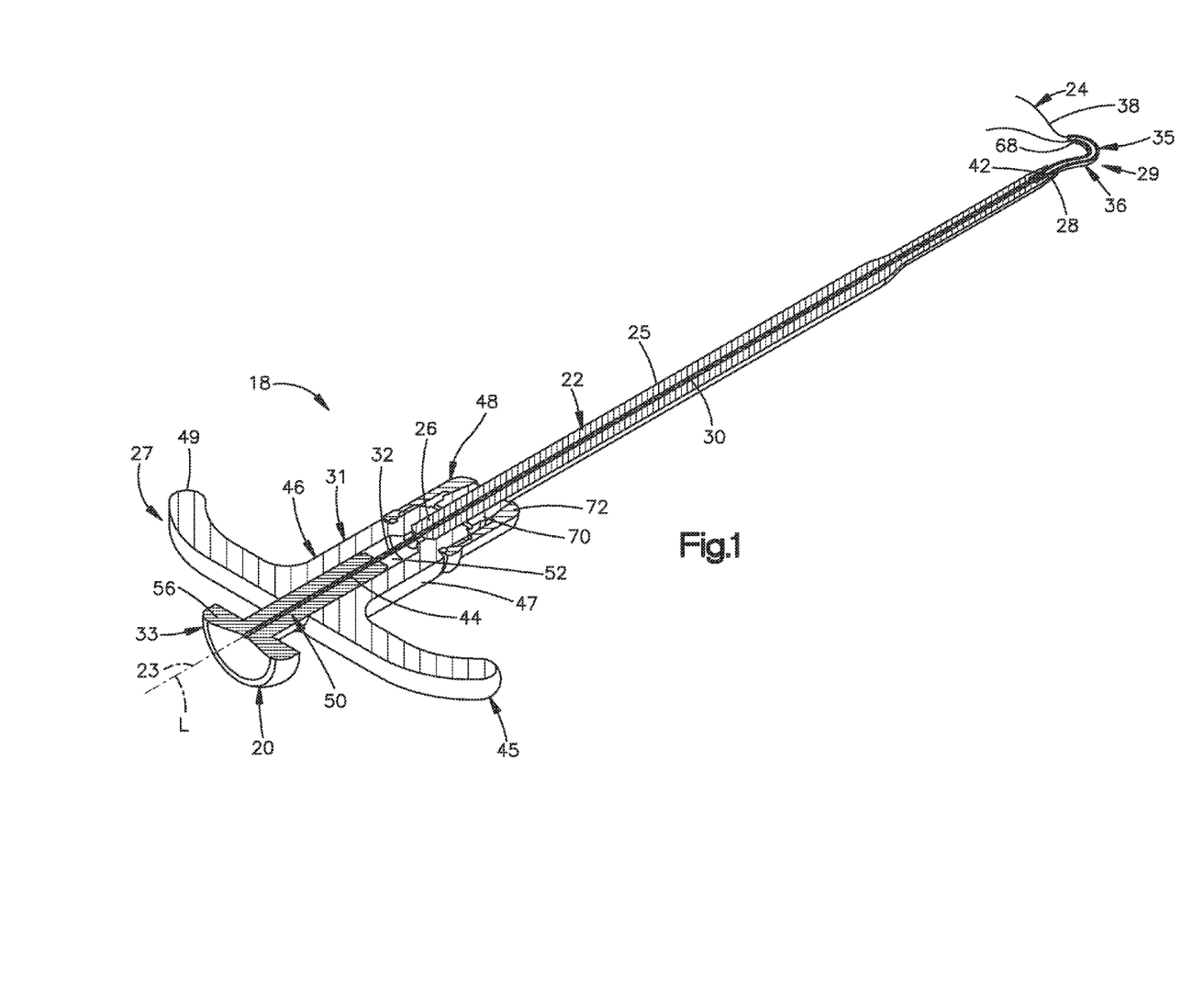
FIG. 1 is a sectional perspective view of a suture device constructed in accordance with one embodiment, showing the suture device in a first retracted configuration.
Figure 2A:
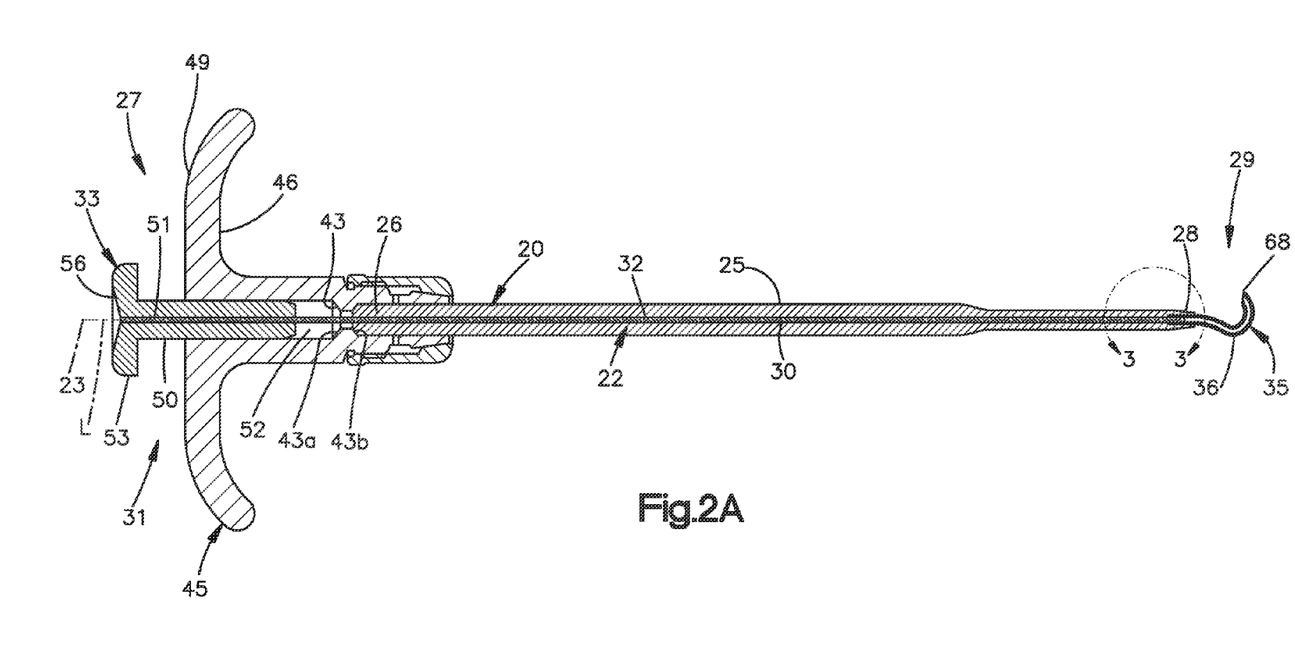
FIG. 2A is a sectional side elevation view of the suture device illustrated in FIG. 1.

Referring to FIGS. 1-2A, a tissue repair assembly 18 includes a suture device 20 and at least one suture thread 24 that is configured to be releasably fixed to the suture device 20, for instance when approximating soft tissue of a patient. The suture device 20 defines a proximal end 27 and a distal end 29 that is opposite the proximal end 27. It should be appreciated that the terms "proximal" and "distal" and derivatives thereof used with respect to the suture device refer to a direction from the distal end 29 toward the proximal end 27, and a direction from the proximal end 27 toward the distal end 29, respectively.

The suture device 20 generally includes a sleeve 22 that extends substantially along a central axis 23, at least a portion of which can extend along a longitudinal direction L, or can extend along any suitable alternative direction as desired. It should be appreciated that the term "longitudinal" and derivatives thereof refer to a direction along or parallel to the longitudinal direction L. The terms "radial," "transverse," and derivatives thereof refer to a direction substantially perpendicular to the central axis 23. The sleeve 22 includes a sleeve body 25 that defines a proximal end 26 and an opposed distal end 28 that is spaced from the proximal end along the central axis 23. Similarly, the suture device 20 defines a proximal end 27 and a distal end 29 opposite the proximal end 27. The sleeve 22 further defines a central opening 30 that extends substantially longitudinally through the sleeve body 25 from the proximal end 26 to the distal end 28. The opening 30 can be cylindrical or any can define suitable alternative shape as desired. The suture thread 24 can be a multifilament or a braided structure, or any alternatively constructed thread.

The suture device 20 includes an actuation assembly 31 that can be disposed at the proximal end 27 of the device 20, and can further include a tip end 35 that can be disposed at the distal end 29 of the suture device 20. Thus, the actuation assembly 31 is disposed proximal with respect to the tip end 35. The tip end 35 can define a cannulated hook 36 that, in turn, can define a distal tip 68 that facilitates movement of the hook 36 through a body tissue wall of a patient and into a body cavity. The distal tip 68 can be acuminate or alternatively shaped as desired. The cannulated hook 36 can be curved in a plane that contains the central axis 23 so that the hook 36 can be passed around a desired body portion of a patient when passing the hook through the tissue.

Figure 5:
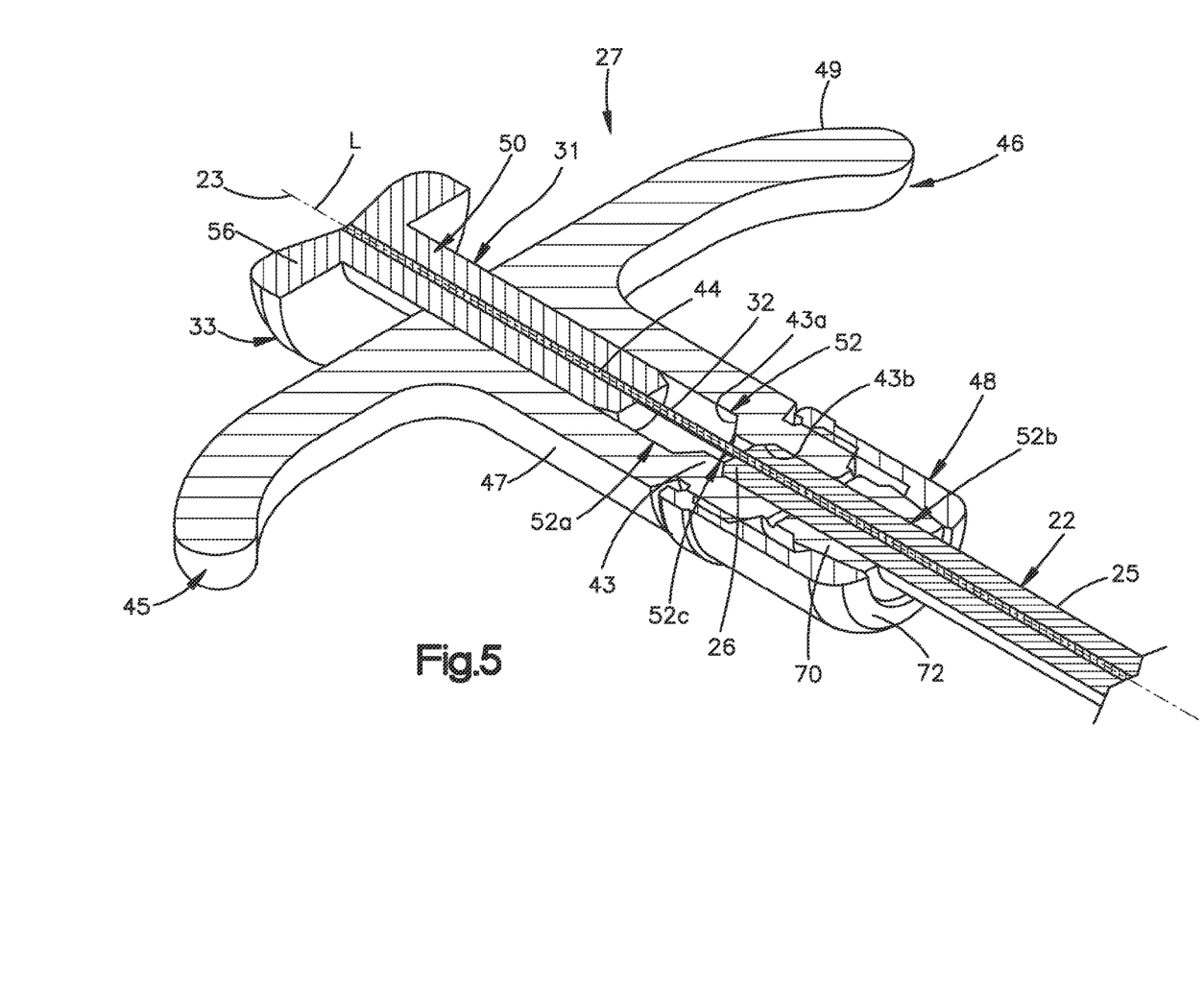
FIG. 5 is an enlarged perspective view of a proximal end of the suture device illustrated in FIG. 1, showing a plunger.

Referring also to FIG. 5, the actuation assembly 31 can include an actuator 33 and a handle assembly 45. The actuator 33 can include a pushbutton 56 and a plunger 32, and is operable to advance a distal end 38 of the suture thread 24 from a location recessed with respect to the distal tip 68, and thus recessed in the suture device 20, to a location that is out, for instance distal, of the suture device 20. Thus, it can be said that the suture device 20 is operable from a first retracted configuration and a second advanced configuration that causes the suture thread 24 to likewise translate between a first retracted position (FIGS. 1-2A) and a second advanced position (FIGS. 2B and 6A-B) that is distal with respect to the first retracted position. For instance, the first retracted position of the suture thread 24 can be recessed with respect to the distal tip 68, and the second advanced position can be distal with respect to the distal tip 68. Alternatively, the first retracted position of the suture thread 24 can be distal with respect to the distal tip 68, and the second advanced position can be disposed further distal with respect to the distal tip 68 than the first retracted position. Thus, the distal end 38 of the suture thread 24 moves distally from the first retracted position to the second advanced position. The handle assembly 45 includes a handle 46 that is configured to be fixedly connected to the sleeve 22, for instance at the proximal end 26, and a fastener 48 that is configured to removably connect the handle 46 to the sleeve 22. Accordingly, the handle 46 is configured as a brace that stabilizes the sleeve 22 as a distal actuation force is applied to the actuator 33, such that distal translation of the actuator 33 causes the suture device 20 to actuate from the first retracted configuration to the second advanced configuration. For instance, a user can grip the handle 46 while simultaneously applying the distal actuation force to the actuator 33, such that the actuator 33 can advance distally with respect to the handle 46. The actuator can likewise receive a proximally directed force that causes the actuator 33 to translate proximally, thereby causing the suture device 20 to iterate from the second advanced configuration to the first retracted configuration. It can thus be said that the suture device 20 is configured to iterated between the first retracted configuration and the second advanced configuration.

The handle 46 includes a stem 47 and a grip 49 that extends longitudinally proximal from, and laterally out from, the proximal end of the stem 47. Thus, the step 47 extends distal from the grip 49. The handle 46 can be substantially T-shaped as illustrated, or can alternatively define any suitable shape as desired. The handle 46 defines an aperture 52 that extends longitudinally through the stem 47 and the grip 49 at a location in alignment with the central opening 30 of the sleeve 22.

The handle 46, and in particular the stem 47, can define a stop member illustrated as a neck 43 that divides the aperture 52 into a first or proximal channel 52A and a second or distal channel 52B. The neck 43 further defines a necked aperture portion 52C of the aperture that is disposed between the proximal and distal channels 52A and 52B, and defines a cross-sectional dimension or diameter less that that of the proximal and distal channels 52A and 52B. In this regard, while various structure can be described herein as defining a diameter, it should be appreciated that the diameter can alternatively be referred to as a cross-sectional dimension, for instance that is not circular. The first channel 52A is configured to receive or otherwise retain the distal end of the push button 56, and the second channel 52B is configured to receive or otherwise retain the proximal end 26 of the sleeve 22. The neck 43 defines a first proximal abutment surface 43A, and a second distal abutment surface 43B.

The fastener 48 is illustrated as a traveler that can be configured as a nut 72 that is threadedly mated with the distal end of the stem 47. Thus, rotation of the nut 72 relative to the stem 47 in a first direction can cause the nut 72 to travel, or translate, proximally along the stem 47. The stem 47 defines a chuck 70 having a ramped surface that abuts a complementary ramped surface of the nut 72. Accordingly, as the nut 72 advances proximally along the distal end of the stem 47, the ramped surfaces of the nut 72 biases the ramped surface of the stem 47 against the sleeve 22, thereby creating a friction fit that fixes the stem 47 to the sleeve 22, thereby removably connecting the handle 46 onto the sleeve 22. For instance, rotation of the nut 72 relative to the stem 47 in a second direction opposite the first direction can cause the nut 72 to travel, or translate, distally along the stem 47, which causes the ramped surface of the nut 72 to be removed from the complementary ramped surface of the stem 47, thereby removing the friction fit of the stem 47 and the sleeve 22. The handle 46 can then be removed from the sleeve 22. It should be appreciated that the handle 46 can be connected to the sleeve in accordance with any suitable alternative embodiment. For instance, the handle 46 can be integral with the sleeve 22.

With continuing reference to FIGS. 1, 2, and 5, the actuator 33 includes a pushbutton 56 and a plunger 32 that is connected, either integrally or discreetly, to the pushbutton 56. In accordance with the illustrated embodiment, the pushbutton 56 defines a grip 53 and a slider 50 that extends distally from the grip. The grip 53 defines a transverse diameter greater than that of the slider 50, and the slider 50 is configured to be slidably received in the first channel 52A of the handle 46. The distal end of the slider 50 can abut the first abutment surface 43A of the stop member 43 to limit the distal travel of the plunger actuator 33 relative to the handle 45 and sleeve 22. Additionally or alternatively, abutment between the distal end of the actuator grip 53 and the proximal end of the handle grip 49 can limit the distal travel of the plunger actuator 33 relative to the handle 45 and sleeve 22. The pushbutton 56 defines an aperture 51 that extends longitudinally through the grip 53 and the slider 50, in alignment with the aperture 52 of the handle 46 and thus also in alignment with the opening 30 of the sleeve 22.

Referring now to FIGS. 1-4A, the plunger 32 includes a plunger body 57 that defines a distal end 42 and a longitudinally opposed proximal end 44. The plunger body 57 has an outer diameter smaller than that of the slider 50, such that the plunger 32 is configured to extend longitudinally through the first channel 52A, the necked channel 52B, and the second channel 52C. The plunger 32 is further sized to be slidably received in the opening 30 in the sleeve 22. The plunger 32 defines a channel 40 that extends longitudinally along the entire length of the plunger body 57, between the distal and proximal ends 42 and 44, respectively. The channel 40 can be substantially U-shaped in cross-section, substantially V-shaped in cross-section, and thus can taper curvedly, conically, nonlinearly, or in any alternative suitable shape from the outer perimeter of the plunger body 57 along a direction toward the central axis 23, such that the channel 40 is configured to receive the suture thread 24.

Figure 4A:
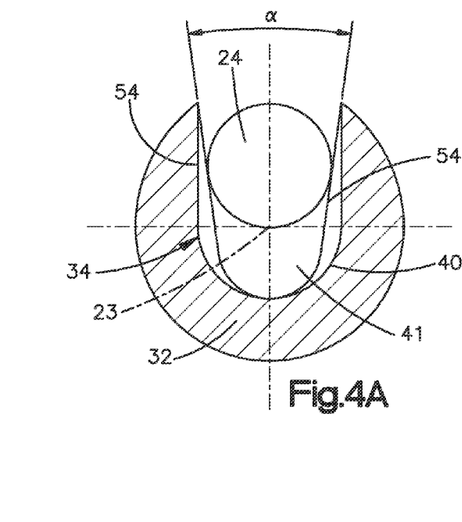
FIG. 4A is a sectional end view of the suture device illustrated in FIG. 3 and taken along line 4A-4A.

In accordance with one embodiment, the plunger 32 defines a clamp 34 that is configured to releasably secure the suture thread 32 to the plunger body 57. In particular, the clamp 34 includes a section 41 of the channel 40 that can define a portion up to all of the channel 40. In accordance with the illustrated embodiment, the section 41 of the channel 40 is disposed proximate to the distal end 42 of the plunger body 57. It should be appreciated that the channel 40 can include more than one clamps 34, for instance proximate to the distal end 42, the proximal end 44, and/or at a location between the distal and proximal ends 42 and 44. The narrowed section 41 of the channel 40 can be substantially V-shaped or substantially U-shaped in cross-section, and thus can taper conically from the outer perimeter of the plunger body 57 towards the central axis 23 so as to define a transverse gap that is less than the cross-sectional dimension of the suture thread 24, so as to releasably retain the suture thread 24.

In accordance with the illustrated embodiment, the clamp 34 includes a pair of opposed side surfaces 54 of the plunger body 57 that define the narrowed section 41 of the channel 40. The side surfaces 54 extend relative to each other and taper toward each other along a direction substantially transverse to the central axis 23. For instance, the side surfaces are tapered toward each other along a direction from the outer perimeter of the plunger body 57 toward the central axis 23 so as to define a gap between the side surfaces 54 that narrows along a direction from the outer perimeter of the plunger body 57 toward the central axis 23. Thus, the side surfaces define an angle α sufficient to cause the suture thread 24 to be wedged by the plunger body 57 in the narrowed section 41 of the channel 40, for instance between the side surfaces 54. For instance, the side surfaces 54 define a transverse dimension therebetween that is less than that of the suture thread 24. Accordingly, the suture thread 24 can be quickly and easily releasably attached to the plunger 32 by imparting a force onto the suture thread 24 that causes the suture thread 24 to move radially inward at the narrowed section 41 of the channel 40. For instance, the suture thread 24 can be inserted into the narrowed section 41 of the channel 40 along the transverse direction, which causes the side surfaces 54 to compress the suture thread 24, thereby capturing the suture thread 24 in the plunger body 57 between the side surfaces 54. The suture thread 24 can likewise be released from the clamp 34 in an easy and quick manner by applying a transverse outward force to the suture thread 24 that dislodges the suture thread 24 from the clamp 34.

The side surfaces 54 can be smooth, or textured so as to assist in retention of the suture thread 24. The angle α can be within a range having an upper end as desired, including approximately 500, or more particularly approximately 400, and a lower end greater than 0°, for instance greater than approximately 20°, such as greater than approximately 300. It should thus be appreciated that the narrowed section 41 can be configured to wedge suture threads of different diameters.

Figure 4B:
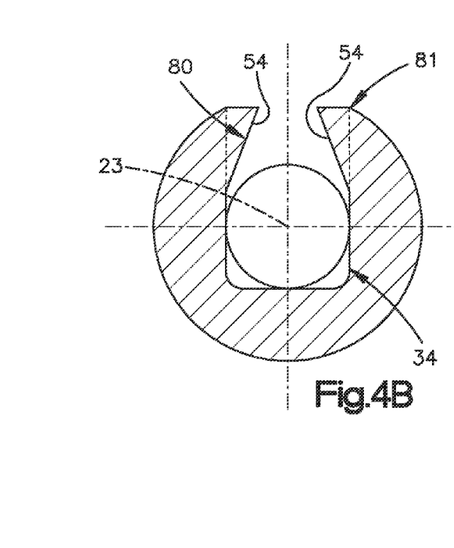
FIG. 4B is a sectional end view similar to FIG. 4A, but constructed in accordance with an alternative embodiment.

In accordance with an alternative embodiment shown in FIG. 4B, the clamp 34 is elastically configured so that the suture thread 24 is clipped into the plunger 32. For instance, the suture thread 24 can be compressed as it is inserted into the clamp 34, and the compression can be reduced or eliminated once the suture thread 24 is fully received in the clamp 34. For instance, the opposed side surfaces 54 of the clamp 34 can taper away from each other along a direction substantially transverse to the central axis 23. For instance, the side surfaces 54 taper away from each other along a direction from the outer perimeter of the plunger body 57 toward the central axis 23. In accordance with one embodiment, the tapered side surfaces 54 can define elastic tongues 80 and 81 that are configured to flex away from each other as the suture thread 24 is inserted into the gap disposed between the side surfaces 54 along a radially inward direction from the outer perimeter of the plunger body 57 toward the central axis 23. Thus, the side surfaces 54 illustrated in FIG. 4B are configured to capture the suture thread 24 in the plunger body 57.

Alternatively still, it should be appreciated that the side surfaces 54 can extend substantially parallel to each other, such that the gap defined between the side surfaces the is sized less than a cross-sectional dimension of the suture thread 24 such that the opposed walls 54 compress the suture thread 24 when the suture thread 24 is disposed in the gap. Thus, it should be appreciated that at least a portion up to all of the gap defined between the opposed side surfaces 54 is sized less than a cross-sectional dimension of the suture thread 24 such that the opposed walls 54 compress the suture thread 24 when the suture thread 24 is disposed in the gap.

Figure 2B:
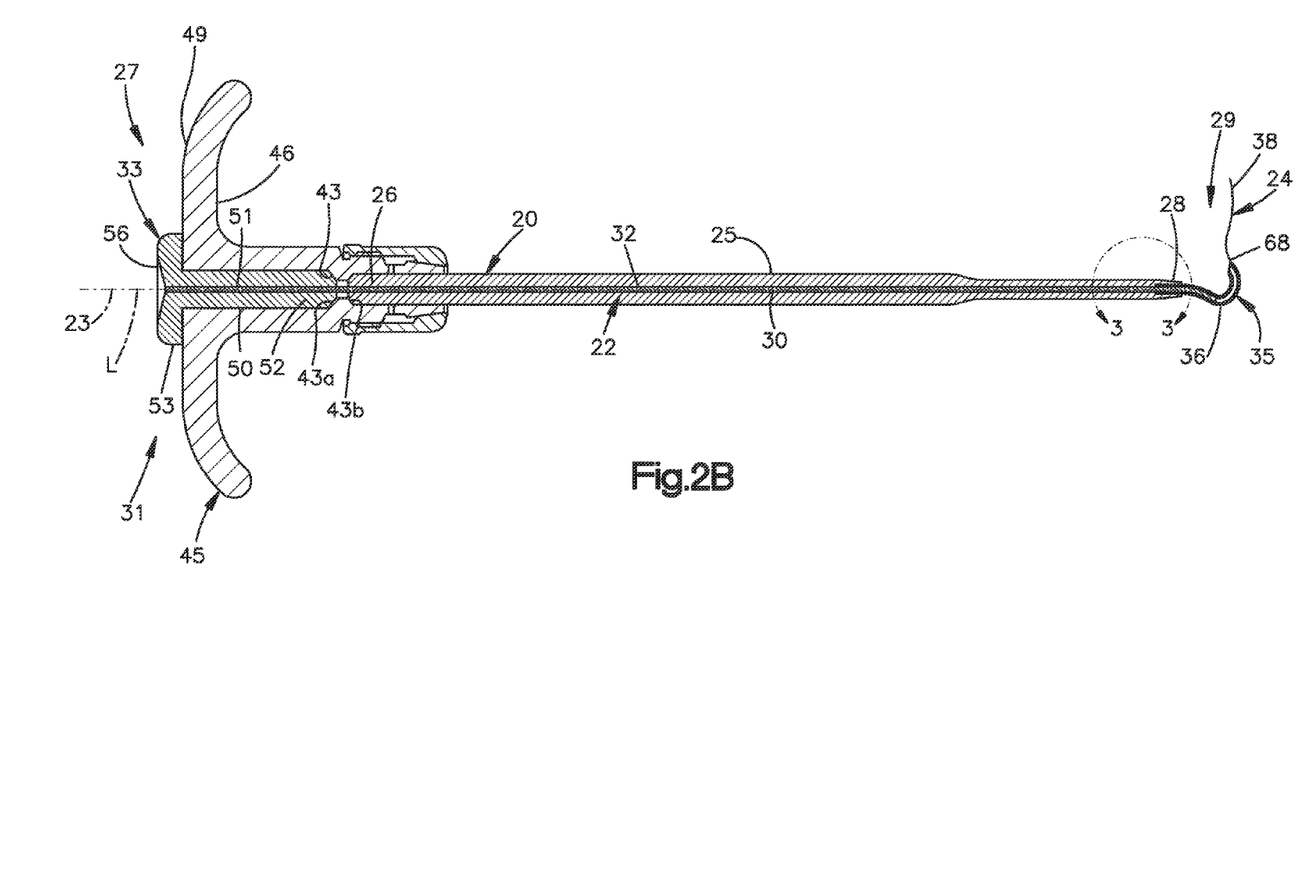
FIG. 2B is a sectional side elevation view of the suture device illustrated in FIG. 2A, but shown in a second advanced configuration.
Figure 3:
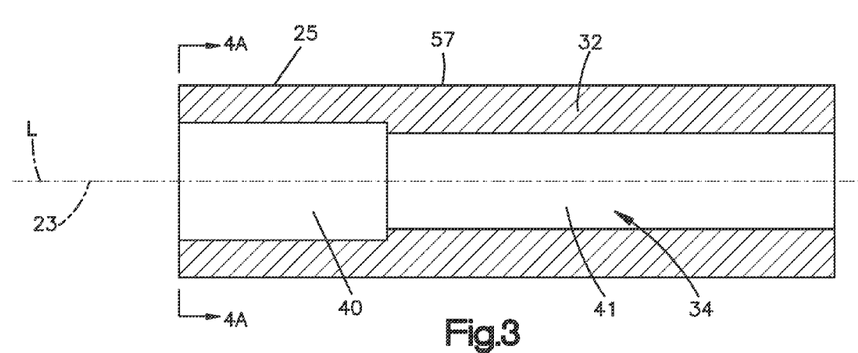
FIG. 3 is an enlarged sectional side elevation view of the suture device illustrated in FIG. 2 and taken along line 3-3.

Referring again to FIGS. 1-2, the device 20 can include a cannulated hook 36 that extends from the distal end 28 of the sleeve 22. The hook 36 can be press-fit into the sleeve 22, overmolded by the sleeve 22, or otherwise attached to the sleeve 22 as desired. For instance, the hook 36 can be integral with the sleeve 22. The cannulation of the hook 36 is aligned with the opening 30 of the sleeve 22, such that when the suture thread 24 is attached to the plunger 32, the suture thread 24 can be passed from the opening 30 in the sleeve 22 into and through the cannulated hook 36. In particular, the plunger 32 can translate distally within the opening 30 of the sleeve 22 toward the hook 36. In accordance with one embodiment, the plunger 32 is inserted into the cannulation of the hook 36 when the actuator 33 is biased distally from a first retracted position to a second advanced position, thereby actuating the suture device 20 from the first retracted configuration to the second advanced configuration. When the plunger 32 is in the first retracted position, the distal end 38 of the suture thread 24 can be recessed from, or disposed proximate with respect to, the distal tip 68 of the hook 36. For instance, the distal end 38 of the suture thread 24 can be disposed proximal with respect to the distal end of the sleeve 22 when the suture device 20 is in the first retracted configuration. When the plunger 32 is biased to the second advanced position, the clamp 34 carries the suture thread 24, and thus causes the suture thread 24 to translate distally to a location whereby the distal end 38 of the suture thread 24 extends out the device 20. For instance, if the device 20 includes the hook 36, the distal end 38 extends from the hook 36 out the suture device 20. If the device does not include a hook 36, then the distal end 38 extends distally from the sleeve 22 out the suture device 20.

Figure 6A:
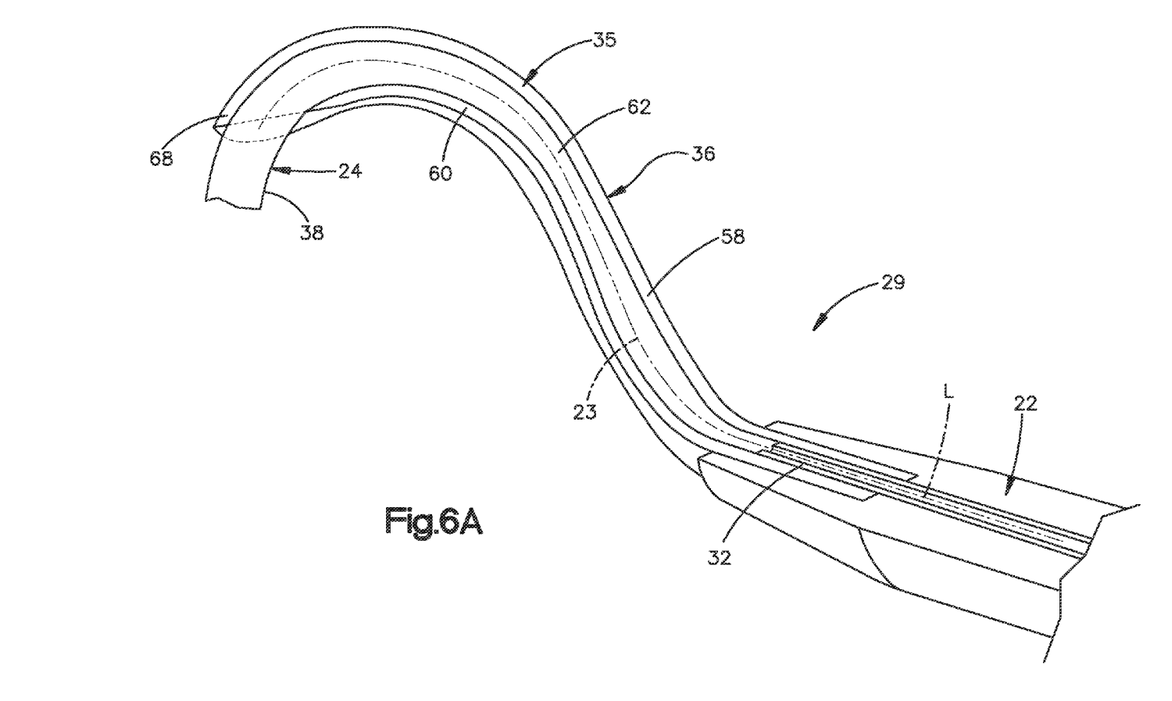
FIG. 6A is an enlarged perspective view of a distal end of the suture device illustrated in FIG. 1, showing the suture device in a second advanced configuration.
Figure 6B:
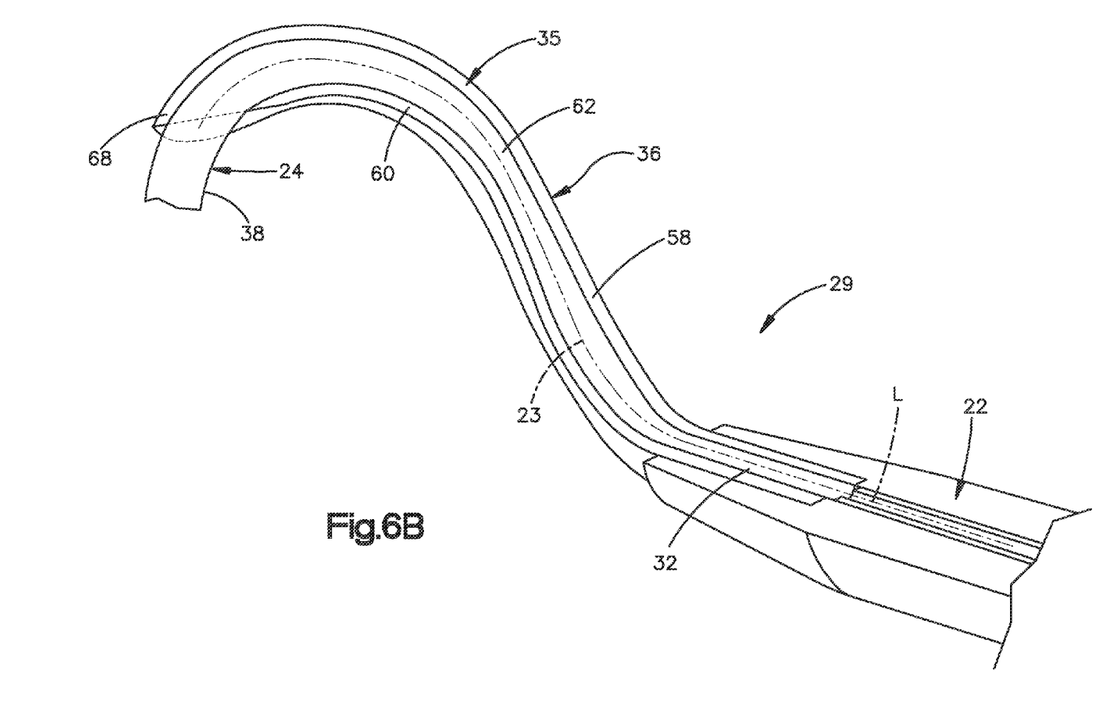
FIG. 6B is an enlarged perspective view of the distal end of the suture device illustrated in FIG. 1 constructed in accordance with an alternative embodiment.

Referring now also to FIGS. 6A-B, the cannulated hook 36 can be curved in more than one plane, such as two planes. For instance, in accordance with the illustrated embodiment, the cannulated hook 36 has a first curved section 58 and a second curved section 60, along a central axis 62 of the cannulated hook 36, which can be coincident with the central axis 23 of the suture device 20. In accordance with the illustrated embodiment, the first curved section 58 lies in a first plane and the second curved section 60 lies in a second plane that is angularly offset with respect to the first plane. The first plane contains the longitudinally extending portion of the central axis 23 of the device 20 and the central axis 62 of the cannulated hook 36. The second plane is angled to the first plane in such a way that the common line of the first and second planes extends orthogonally to the longitudinal direction L. Thus, the hook 36 can be helically curved, which can be advantageous when performing shoulder surgery, in particular surgery on the rotator cuff or the meniscus, where limited anatomical space is available to move the tip end 35 of the device 20.

As described above, the slider 50 is connected to the proximal end 44 of the plunger 32 and has a greater diameter than the plunger 32. The plunger 32 can be slim, and can have an outer cross-sectional dimension smaller than that of the opening 30 of the sleeve 22. The slider 50 fits snugly in the proximal channel 52A defined by the aperture 52 of the handle 46. Thus the handle 46, and in particular the aperture 52 defines a guide member that causes the slider 50, and thus the plunger 23, to translate along the central axis 23. Alternatively, the outer cross-sectional dimension of the plunger 23 can be substantially equal to that of the opening 30 of the sleeve 22. Further, the slider 50 comprises a push button 56 arranged at its rearward end so that the actuation assembly 31 has a syringe like design that provide an ergonomically friendly actuator for the user. For instance, the user can brace two fingers under the grip 49 of the handle 46, and depress the pushbutton 56 by applying a distal biasing force to the grip 53 of the pushbutton 56 with his or her thumb.

During operation, the suture thread 24 is affixed to the plunger 32, for instance by capturing the suture thread 24 in the clamp 34 in the manner described above, and the plunger 32 is inserted longitudinally into the opening 30 of the sleeve 22. Thus, the actuator 33, and also the plunger 32 which is attached to the actuator 33, is in a first retracted position. When the plunger 32 is in the first retracted position, the distal end 38 of the suture 24 does not extend out the device 20 in accordance with one embodiment. For instance, when the plunger 32 is in the first retracted position, the distal end 38 of the suture thread 24 can be disposed in the sleeve, and can reach the distal end 28 of the sleeve 22, or can alternatively extend into the cannulated hook 36.

The cannulated hook 36 can then be guided to a desired position within a body portion of a patient until the tip 68 of the hook 36 is in a desired position, such as a cavity within the patient's body. The cavity can be a natural anatomical cavity, or can be created through the retraction of tissue. Next, the plunger 32, and thus also the actuator 33, is advanced distally from the first retracted position to the second advanced configuration, for instance until the slider 50 abuts the proximal abutment surface 43A of the neck 43. As illustrated in FIG. 6A, the plunger 32 can extend into the cannulation of the hook 36 when the actuator 33 and the plunger 32 are in the respective second advanced positions. It should be appreciated that the plunger 32 can be disposed proximal with respect to the cannulated hook 36 when the actuator 33 and the plunger 32 are in the respective first retracted positions, or alternatively the plunger 32 can be extend into the cannulation of the cannulated hook 36 when the actuator 33 and the plunger 32 are in the respective first retracted positions, and the plunger 32 can extend further into the cannulation of the cannulated hook 26 when in the second advanced position.

Alternatively still, as illustrated in FIG. 6B, the plunger 32 can terminate at a location proximal with respect to the cannulation of the hook 36 when the actuator 33 and the plunger 32 are in the respective second advanced configurations. Whether the plunger 32 is disposed in the cannulation of the hook 36 or is disposed proximal of the hook 36 when the plunger 32 is in the second advanced configuration, the suture thread 24 is guided such that the distal end 38 is translated out the device 20 as the plunger 32 is actuated from the first retracted position to the second advanced position. For instance, the distal end 36 of the suture strand 24 can extend distally out the sleeve 22, and in accordance with one embodiment can extend distally out the cannulated hook 36 when the plunger 32, and thus the suture thread 24, advances from the first retracted position to the second advanced position.

In accordance with one embodiment, the distal end 38 of the suture thread 24 can protrude any distance out the suture device 20 as desired, for instance between approximately 1 cm and 2 cm out the device 20. Thus, the distal end 38 of the suture thread 24 can be grasped by another instrument, such as a clamp, and the suturing procedure can be completed. Thus, the suture device 20 can pass the suture thread 24 through soft tissue of a patient and subsequently insert the distal end 38 into a target location, such as a cavity within a patient's body, in a quick and easy manner.

Accordingly, a method is provided for inserting the suture thread 24 into a body portion of a patient using the suture device 20. The method includes the step of attaching the suture thread 24 to the plunger 32 such that a distal end 38 of the suture thread 32 protrudes from the distal end of the plunger 32. The plunger 32 is placed in the opening 30 of the sleeve 22 in a first retracted position, whereby the distal end 38 of the suture thread 32 can be disposed proximal of the distal tip 68 of the hook 36. For instance, the distal end 38 of the suture thread 32 can be disposed in the cannulation of the hook 36 or can be disposed in the opening 30 of the sleeve 22, for instance at the distal end 28, when the plunger 32 is in the first retracted position. The plunger 32 can then be depressed distally, for instance by applying a manual biasing force onto the push button 56, thereby advancing the plunger 32 from the first retracted position to a second advanced position, which causes the plunger 32 to eject the distal end 38 of the suture thread 24 distally out the device 20. For instance, the distal end of the plunger body 57 can extend to a location in the cannulation of the hook 36, or to a location proximal of the hook 36, when the plunger 32 is in the second advanced position. The distal end 38 of the suture thread 24 can be extend out the suture device 20 when the plunger 32 is in the second advanced position. For instance, the suture thread 24 can extend distal with respect to the sleeve, and can further extend distal with respect to the cannulated hook 36, for instance when the suture device 20 includes the cannulated hook 36. The distal end 38 of the suture thread 24 can then be picked up with any suitable instrument, such as a clamp, to complete the suturing procedure. For instance, the instrument can grasp the suture thread 24 and place the suture thread in sufficient tension that causes the suture thread 24 to be dislodged from the clamp 34 and free the suture thread 24 for further distal translation with respect to the suture device 20.

In embodiments where the sleeve 22 is connected to the hook 36, the hook 36 can be driven and guided into soft tissue of the patient's body when inserting the device 20 the body. Thus when the hook 36 is in a desired location, the plunger 32 can eject the distal end 38 of the suture thread 24 distally out the hook 36. In embodiments where the suture device 20 does not include the hook 36, for instance when inserting the suture thread 24 to an anatomical location that defines an anatomically natural void, the distal end 38 of the suture thread can be picked up with any suitable instrument once the distal end 38 extends distal with respect to the sleeve 22.

In accordance with one embodiment, a tissue repair kit can include at least one sleeve 22, at least one handle 46 that is connected or configured to be connected to the proximal end of the sleeve 22, at least one plunger 32, and at least one hook 36 that is connected or configured to be connected to the sleeve 22. For instance, the kit can include a plurality of differently shaped hooks 36. The different shapes can include one or more curves in a common plane or in multiple planes, and/or can further include differently shaped tips, e.g. straight/bent to the right/bent to the left so that the device can be adapted to a particular use. In instances where the hook 36 is connected to the sleeve 22 as manufactured, the sleeve 22 can be coupled to the handle 46 as desired. The kit can further include a plurality of suture threads 24, each having different diameters that are configured to be releasably fixed to the suture device 20, and in particular the plunger 32.

Although the invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments described herein. Furthermore, it should be appreciated that apparatus and methods described in connection with one embodiment can be equally applicable to all other embodiments unless otherwise indicated. One of ordinary skill in the art will readily appreciate from the present disclosure that apparatus and methods presently existing or later to be developed that perform substantially the same function or achieve substantially the same result as the corresponding embodiments described herein may be utilized according to the present invention. Thus, it will be appreciated by those skilled in the art that various modifications and alterations of the invention can be made without departing from the broad scope of the appended claims. Some of these have been discussed above and others will be apparent to those skilled in the art.

What is claimed is:

1. A tissue repair kit configured to guide a suture thread through tissue, the kit comprising:
    at least one sleeve including a sleeve body that is elongate along a central axis, the sleeve body defining a proximal end, a distal end spaced from the proximal end along the central axis in a distal direction, and an opening that extends along the central axis between the proximal end and the distal end;
    at least one cannulated hook separate from and configured to be coupled to the distal end of the at least one sleeve so that a cannulation of the at least one cannulated hook is open to the opening of the at least one sleeve, wherein the at least one cannulated hook includes a distal tip that defines an exit of the cannulation;
    at least one plunger configured to attach to a portion of the suture thread, the at least one plunger configured to be slidably inserted into the opening of the at least one sleeve, wherein the at least one plunger includes a portion configured to capture the portion of the suture thread so as to releasably attach the portion of the suture thread to the at least one plunger, wherein when 1) the at least one cannulated hook is coupled to the distal end of the at least one sleeve, and 2) the at least one plunger is slidably disposed in the opening of the at least one sleeve, the at least one plunger is moveable along the distal direction to advance the portion of the suture thread attached to the at least one plunger into the at least one cannulated hook; and
    a stop member configured to prevent movement of the at least one plunger in the distal direction when 1) the at least one plunger is slidably inserted into the opening, and 2) the portion of the at least one plunger is proximal of the distal tip.

2. The kit of claim 1, wherein the at least one plunger is moveable in the distal direction from a first retracted position where the at least one plunger and the portion of the suture thread are spaced from the cannulated hook to a second advanced position where the at least one plunger and the portion of the suture thread extend into the at least one cannulated hook.

3. The kit of claim 1, wherein the at least one plunger includes a plunger body that extends along the central axis when the at least one plunger is disposed in the respective opening, the plunger body defining a plunger proximal end, a plunger distal end spaced from the plunger proximal end along the central axis, and a channel that extends from the plunger body proximal end to the plunger body distal end.

4. The kit of claim 3, wherein the plunger body further defines a clamp at the portion of the at least one plunger, the clamp including a pair of opposed surfaces that are configured to capture the portion of the suture thread so as to releasably attach the portion of the suture thread to the at least one plunger.

5. The kit of claim 3, wherein the sleeve body defines a sleeve length that extends from the proximal end to the distal end, and the plunger body defines a plunger length that extends from the plunger proximal end to the plunger distal end, wherein the plunger length is greater than the sleeve length.

6. The kit of claim 1, wherein the at least one hook is a plurality of cannulated hooks, each one of the plurality of the cannulated hooks configured to be attached to the distal end of the at least one sleeve, wherein each one of the plurality of cannulated hooks defines a different shape than every other one of the plurality of cannulated hooks.

7. The kit of claim 6, wherein one of the plurality of cannulated hooks is acuminate.

8. The kit of claim 6, wherein one of the plurality of cannulated hooks is curved in at least one plane.

9. The kit of claim 6, wherein one of the plurality of cannulated hooks includes a first curved section and a second curved section, wherein the first curved section lies in a first plane and the second curved section lies in a second plane that is angularly offset with respect to the first plane.

10. The kit of claim 6, wherein one of the plurality of cannulated hooks includes a first straight section and a second curved section, wherein the first straight section lies in a first plane and the second curved section lies in a second plane that is angularly offset with respect to the first plane.

11. The kit of claim 6, wherein one of the plurality of cannulated hooks defines a helical shape.

12. A tissue repair kit configured to guide a suture thread through tissue, the kit comprising:
    at least one sleeve including a sleeve body that is elongate along a central axis, the sleeve body defining a proximal end, a distal end spaced from the proximal end along the central axis in a distal direction, and an opening that extends along the central axis between the proximal end and the distal end;
    a cannulated hook attached to the at least one sleeve, such that 1) the cannulated hook extends from the sleeve in the distal direction, and 2) a cannulation of the hook is open to the opening of the at least one sleeve; and
    at least one plunger including a plunger body that extends from a plunger proximal end in the distal direction and terminates at a plunger distal end, and a portion disposed between the plunger proximal end and the plunger distal end that is configured to attach to a portion of the suture thread, the at least one plunger configured to be slidably inserted into the opening of the at least one sleeve such that 1) the plunger is slidable in the opening of the at least one sleeve in the distal direction to advance the portion of the suture thread attached to the at least one plunger into the cannulated hook, and 2) the at least one plunger is moveable in the distal direction from a first retracted position to a second advanced position, such that in the second advanced position a) movement of the at least one plunger in the distal direction is blocked, and b) the plunger distal end is positioned either within the cannulation or within the opening.

13. The kit of claim 12, wherein the portion of the at least one plunger is further slidable from the opening of the at least one sleeve into the cannulation of the cannulated hook.

14. The kit of claim 12, wherein the at least one sleeve is a plurality of sleeves, and the cannulated hook is a plurality of cannulated hooks, each hook being attached to a respective one of the plurality of sleeves, wherein each one of the plurality of cannulated hooks defines a different shape than every other one of the plurality of cannulated hooks.

15. The kit of claim 14, wherein the plunger body extends along the central axis when the plunger is disposed in the opening, and the plunger body defines a channel that extends from the plunger body proximal end to the plunger body distal end.

16. The kit of claim 12, further comprising at least one handle that includes a rear end and an opposed front end, the front end configured to be coupled to the proximal end of the at least one sleeve.

17. A method for assembling a suture device configured to guide a suture thread through tissue, the method comprising the steps of:
clamping the suture thread to at least one plunger such that a free portion of the suture thread protrudes from a distal end of the at least one plunger that is spaced from a proximal end of the at least one plunger along a central axis in a distal direction;
inserting the at least one plunger into an elongate opening of a sleeve such that the clamped suture thread is movable with the at least one plunger along the central axis between a) a first retracted position where the free portion of the suture thread is disposed in the sleeve, and b) a second advanced position in which the free portion of the suture thread extends out of the elongate opening and into a cannulation of at least one cannulated hook when the at least one cannulated hook is coupled to the sleeve; and
after the inserting step, coupling the at least one cannulated hook to the sleeve such that the cannulation of the at least one cannulated hook is open to the elongate opening of the sleeve.

18. The method of claim 17, further comprising the step of advancing the at least one plunger in the distal direction until further advancement is stopped by interference with a stop member, such that when further advancement is stopped by interference with the stop member a portion of the at least one plunger that is clamped to the suture thread is positioned within the at least one cannulated hook.

19. The method of claim 17, further comprising the step of advancing the at least one plunger in the distal direction until further advancement is stopped by interference with a stop member, such that when further advancement is stopped by interference with the stop member a portion of the at least one plunger that is clamped to the suture thread is positioned within the elongate opening of the sleeve.

* * * * *